United States Patent
Hale

(10) Patent No.: US 11,950,758 B2
(45) Date of Patent: *Apr. 9, 2024

(54) VIDEO CAMERA HAVING VIDEO IMAGE ORIENTATION BASED ON VECTOR INFORMATION

(71) Applicant: KARL STORZ Imaging, Inc., Goleta, CA (US)

(72) Inventor: Eric L. Hale, Vancouver, WA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 384 days.

This patent is subject to a terminal disclaimer.

(21) Appl. No.: 17/337,188

(22) Filed: Jun. 2, 2021

(65) Prior Publication Data

US 2021/0289146 A1 Sep. 16, 2021

Related U.S. Application Data

(63) Continuation of application No. 16/665,744, filed on Oct. 28, 2019, now Pat. No. 11,039,085.

(51) Int. Cl.
*A61B 1/00* (2006.01)
*H04N 5/262* (2006.01)
*H04N 7/18* (2006.01)

(52) U.S. Cl.
CPC ...... *A61B 1/00009* (2013.01); *A61B 1/00006* (2013.01); *H04N 5/2628* (2013.01); *H04N 7/183* (2013.01)

(58) Field of Classification Search
None
See application file for complete search history.

(56) References Cited

U.S. PATENT DOCUMENTS

| | | |
|---|---|---|
| 6,241,657 B1 | 6/2001 | Chen |
| 6,346,940 B1 | 2/2002 | Fukunaga |
| 6,471,637 B1 | 10/2002 | Green |
| 6,511,418 B2 | 1/2003 | Shahidi |
| 6,663,559 B2 | 12/2003 | Hale |
| 6,916,286 B2 | 7/2005 | Kazakevich |
| 7,585,273 B2 | 9/2009 | Adler |

(Continued)

FOREIGN PATENT DOCUMENTS

WO 0174266 A1 10/2001

OTHER PUBLICATIONS

T. Nguyen, et al., Reduced-complexity entropy coding of transform coefficient levels using a combination of VLC and PIPE, Input Document, Joint Collaborative Team on Video Coding (JCT-VC) of ITU-T SGI6 WP3 and ISO/IEC JTC1/SC29/WG11 Doc. No. JCTVC-D336 (Jan. 21, 2011) (Year: 2011).*

(Continued)

*Primary Examiner* — Lindsay J Uhl
(74) *Attorney, Agent, or Firm* — David N. Villalpando; Honigman LLP

(57) ABSTRACT

A camera configured to maintain an image in a preferred orientation when the camera is passed from one user to another is provided. The camera detects a spatial orientation of the camera in at least a first position. The camera detects a vector information generated when the camera is passed from one user to another. The camera processes the spatial orientation and vector information so as to retain the image in a preferred orientation.

17 Claims, 6 Drawing Sheets

(56) References Cited

U.S. PATENT DOCUMENTS

| | | |
|---|---|---|
| 7,824,328 B2 | 11/2010 | Gattani |
| 7,956,887 B2 | 6/2011 | Hoeg |
| 9,375,133 B2 | 6/2016 | Kitamura |
| 11,039,085 B2 * | 6/2021 | Hale .................. G02B 23/2484 |
| 2005/0228230 A1 | 10/2005 | Schara |
| 2008/0159653 A1 * | 7/2008 | Dunki-Jacobs ........ A61B 5/067 |
| | | 382/293 |
| 2014/0029837 A1 | 1/2014 | Venkatraman |

OTHER PUBLICATIONS

Artikis, T.; Extended European Search Report, dated Feb. 23, 2021 pp. 1-7 Munich, Germany Application No. 20204128.1-1122.

* cited by examiner

US 11,950,758 B2

VIDEO CAMERA HAVING VIDEO IMAGE ORIENTATION BASED ON VECTOR INFORMATION

TECHNICAL FIELD

This disclosure relates to a camera configured retain a digital image in an upright manner based upon vector information.

BACKGROUND

Cameras provide an image based upon the orientation of the camera. As an example, without any correction, a video image will rotate with the rotation of a video camera. In some embodiments, the physical dimension of the camera provides the user with a visual indicator to ensure the video image is oriented in a desired orientation. For instance, it is easy to capture a video image from a video camera that is rectangular in a predetermined orientation as it is easily recognizable when the camera is upright. However, in certain applications, such as an endoscope, it is difficult to determine when the endoscope is upright as the endoscope is generally cylindrical. Further, the orientation of the video image may rotate when the endoscope is handed from one person or another, such as from the nurse to the surgeon.

An example will be described with reference to FIGS. 1A through 2B. FIG. 1A depicts a surgical procedure with a nurse 200 and a surgeon 300 standing over a patient 400. FIG. 1A shows the nurse 200 holding an endoscope 10. The nurse 200 turns on the endoscope 10 and levels the endoscope 10. As used herein, the term level means rotating the video image on the display to a desired orientation. The nurse 200 may rotate the grip of the endoscope 10 to an upright orientation so that outside of the surgical site, the video image is aligned with the orientation of the physical space. That is, the patient 400 is shown on the video display as being generally centered, as shown in FIG. 1B. Alternatively, an actuator, such as a button, may be pressed to rotate the video image. Once the video image is leveled (as shown in corresponding FIG. 1B), the nurse 200 sets the level by pressing a button.

FIG. 2A is a depiction of FIG. 1A after the nurse 200 has handed the endoscope 10 to the surgeon 300. When the endoscope 10 is handed over, the surgeon 300 may grip the endoscope 10 in a different orientation. In particular, the longitudinal length of the endoscope 10 extends along an axis which is different than that shown in FIG. 1A. Additionally, the endoscope 10 is positioned within the room in a different location along X, Y and Z axes. It should be appreciated that the endoscope 10 may have a common point(s) along any one of the X, Y and Z axis, but at least one of the points is different. Further, the endoscope 10 may be rotated about its longitudinal length. As such, what was level for the nurse 200 may not be level for the surgeon 300, as shown by the corresponding image depicted in FIG. 2B which shows the patient 400 being angled relative to FIG. 1B. This requires the surgeon 300 to level the video image again.

Accordingly, it remains desirable to have a video camera configured to automatically orient the video image to a preferred orientation.

SUMMARY

One aspect of the disclosure provides a camera configured to display an image onto a display unit. The camera includes a camera head unit and an orientation unit. The camera head unit is configured to capture image data. The orientation unit is configured to detect a spatial orientation of the camera head unit. The orientation unit is also configured to detect a vector information of the camera head unit. A first input is configured to record the spatial information of the video image.

The camera further includes a display control unit. The display control unit is configured to process the spatial orientation recorded by the first input and the vector information so as to retain an orientation of the video image as the camera head unit is moved. For example, the orientation of the video image may be retained in an upright position as the camera is passed from a nurse to a surgeon.

In one aspect, the camera includes an endoscope attached to the camera head unit, and the display control unit is further configured to process the image data so as to generate a video image.

In another aspect of the camera, the orientation unit is configured to detect at least one of an acceleration or a gravitational relationship of the camera head unit. The orientation unit may include an accelerometer and/or a gyroscope sensor. The orientation unit detects an acceleration and/or a gravitational relationship of the camera and transmits the detected acceleration and/or gravitational relationship to the display control unit. The display control unit processes the acceleration and/or gravitational relationship to determine the vector information.

In another aspect of the camera, the camera includes a second input. The second input is configured to manually adjust the orientation of the video image so as to define an adjusted video orientation. The display control unit is further configured to retain the video image in the adjusted video orientation.

Another aspect of the disclosure provides a video imaging system. The video imagining system is configured to display a video image onto a display unit. The video imagining system includes a camera head unit and an orientation unit. The camera head unit is configured to capture image data and process the image data so as to generate a video signal. The orientation unit is configured to detect a spatial orientation of the camera head unit. The orientation unit is also configured to detect a vector of the camera head unit. A first input is configured to record the spatial information of the video image.

The video imaging system further includes a display control unit. The display control unit is configured to process the video signal for display on the display unit. The display control unit is further configured to process the spatial orientation recorded by the first input and the vector information so as to retain an orientation of the video image as the camera head unit is moved. For example, the orientation of the video image may be retained in an upright position as the camera is passed from a nurse to a surgeon.

In one aspect of the video imagining system, the orientation unit is configured to detect at least one of an acceleration or a gravitational relationship of the camera head unit. The orientation unit may include an accelerometer and/or a gyroscope sensor. The orientation unit detects an acceleration and/or a gravitational relationship of the camera and transmits the detected acceleration and/or gravitational relationship to the display control unit. The display control unit processes the acceleration and/or gravitational relationship to determine the vector information.

In another aspect of the video imaging system, the camera includes a second input. The second input is configured to manually adjust the orientation of the video image so as to define an adjusted video orientation. The display control unit is further configured to retain the video image in the adjusted video orientation.

Another aspect of the present disclosure provides a method for maintaining an orientation of a video image on a display unit in an upright position when a video camera is being handed from a first person to a second person. The method includes the step of pointing the video camera at an end user position and recording a spatial orientation of the video camera when the video camera is pointed at the end user position so as to define a first spatial orientation. The method includes the step of pointing the video camera at a surgical site and recording the spatial orientation of the video camera when the video camera is pointed at the surgical site so as to define a second spatial orientation. The method includes the step of handing the video camera to the second person, and determining a vector information of the video camera as the video camera is handed to the second person. A display control unit is configured to process the first spatial orientation, the second spatial orientation and the vector information so as to maintain the video image in the upright position.

In one aspect of the method, the method is determined by an acceleration and/or gravitational relationship of the video camera.

In another aspect of the method, the method may further include the step of holding the video camera in a use position and recording the spatial orientation of the video camera when the video camera is in the use position so as to define a third spatial orientation. The display control unit is further configured to process the third spatial orientation so as to maintain the video image in the upright position.

The details of one or more implementations of the disclosure are set forth in the accompanying drawings and the description below. Other aspects, features, and advantages will be apparent from the description and drawings, and from the claims.

DESCRIPTION OF DRAWINGS

Like reference symbols in the various drawings indicate like elements.

DETAILED DESCRIPTION

A camera configured to maintain an image in a preferred orientation when the camera is passed from one user to another is provided. The camera detects a spatial orientation of the camera in at least a first position. The camera detects a vector information generated when the camera is passed from one user to another. The camera processes the spatial orientation and vector information so as to retain the image in a preferred orientation.

Figure 1A:
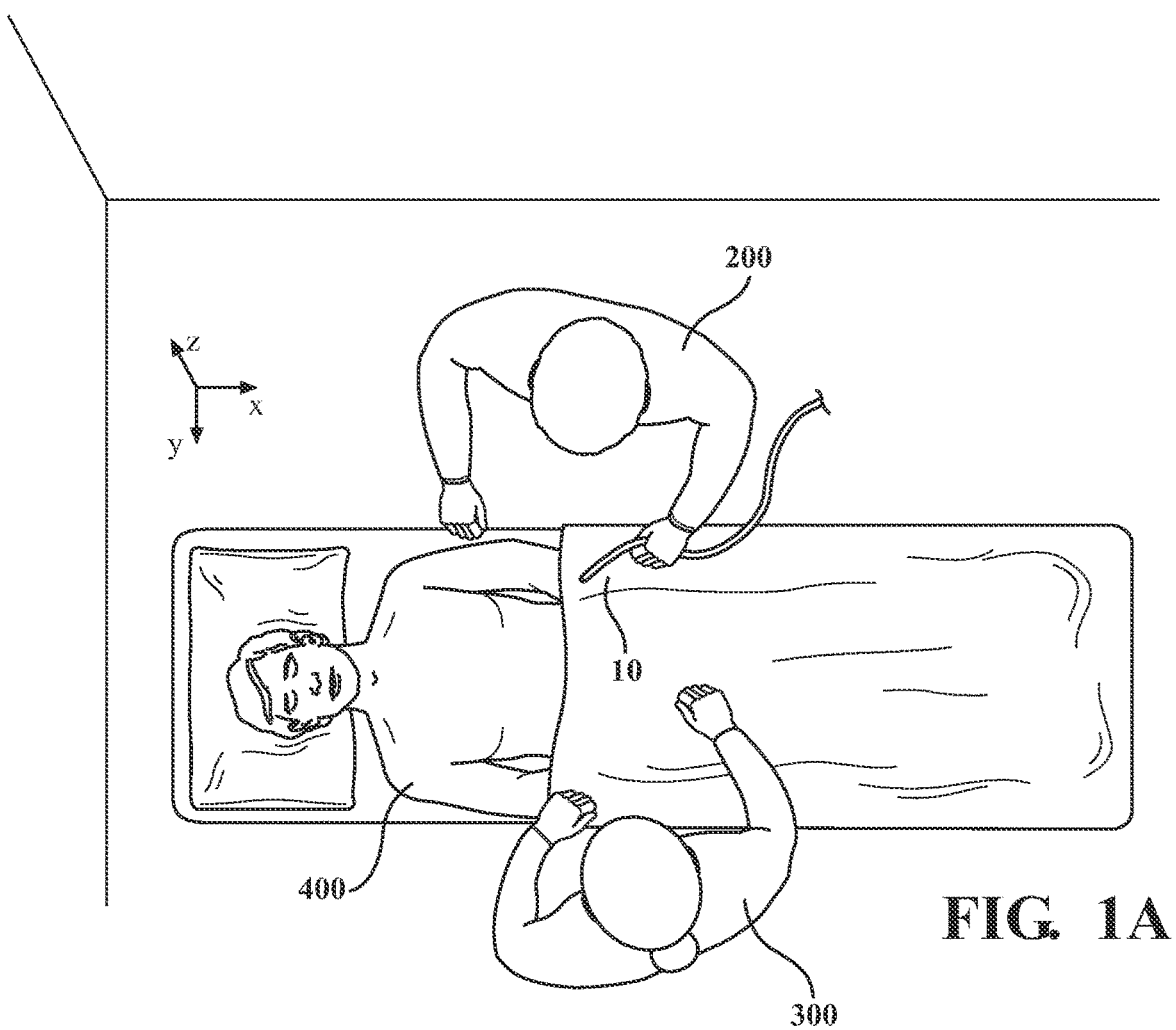
FIG. 1A is a depiction showing a nurse holding an endoscope in a surgery room.
Figure 1B:
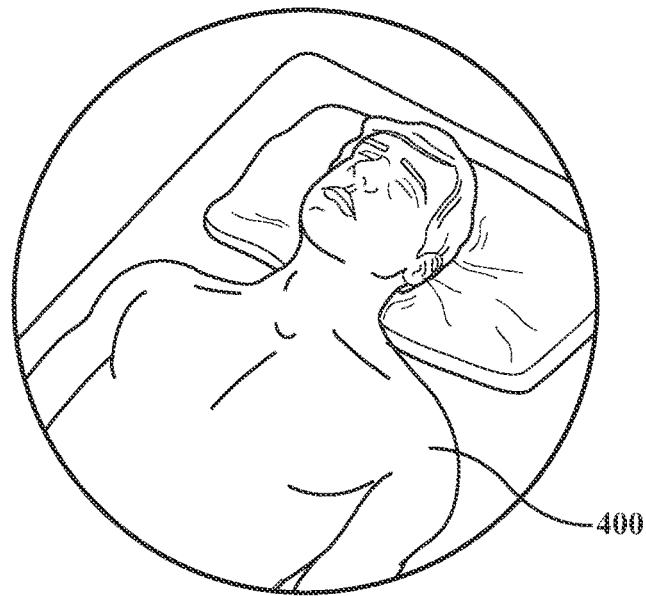
FIG. 1B is a depiction of the video image of the endoscope shown in FIG. 1A.
Figure 2A:
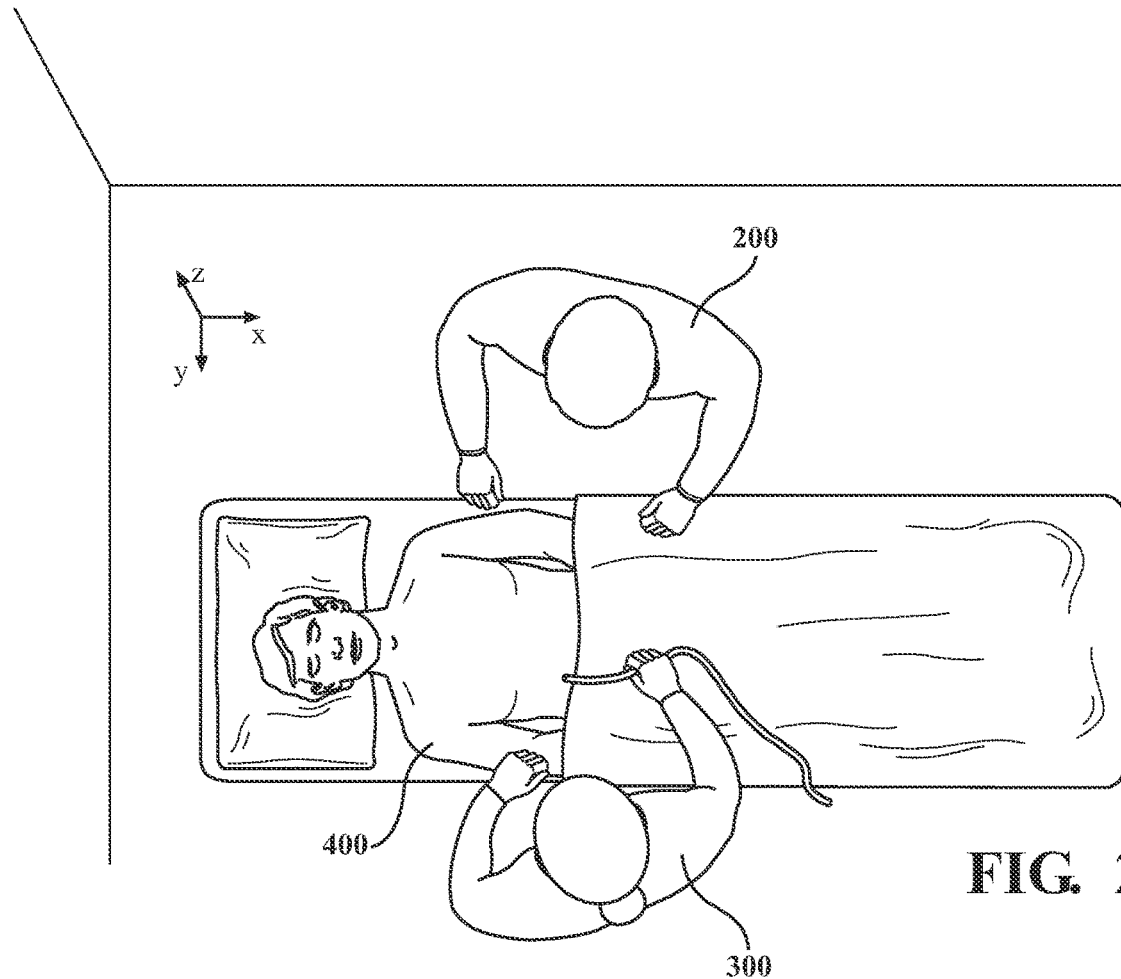
FIG. 2A is a depiction showing a surgeon holding the endoscope.
Figure 2B:
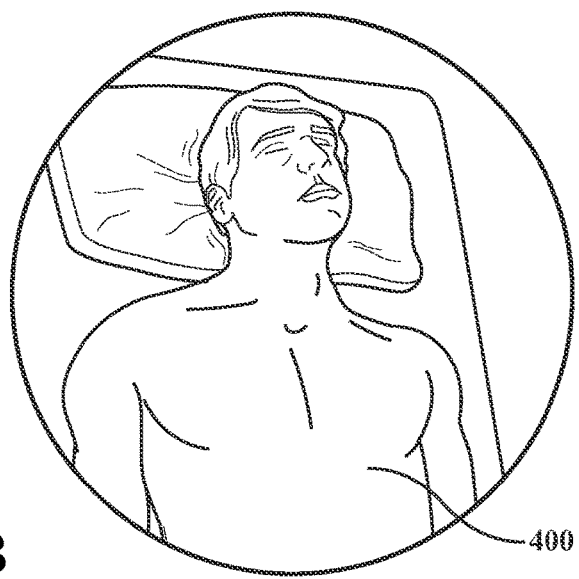
FIG. 2B is a depiction of the video image of the endoscope shown in FIG. 2A.
Figure 3:
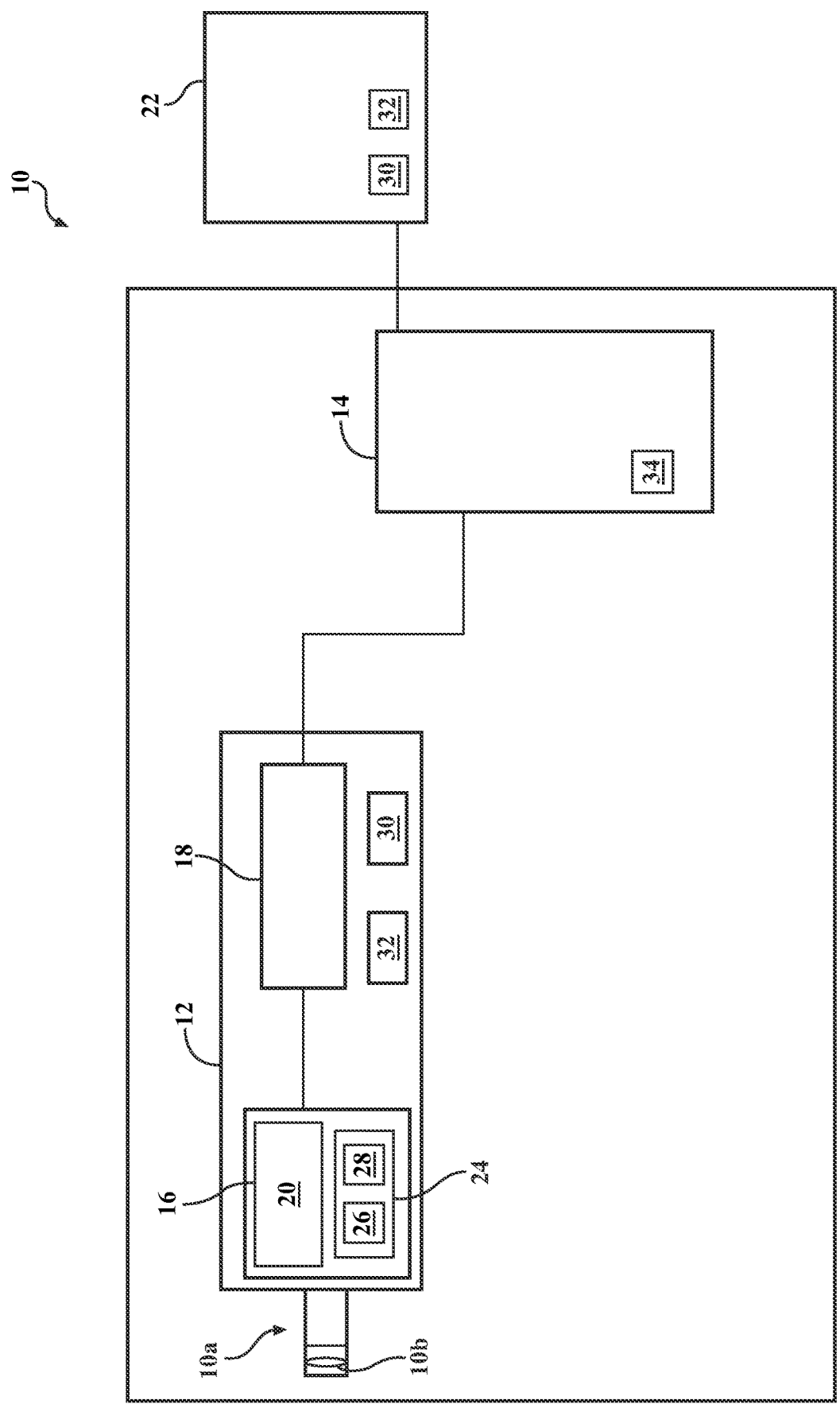
FIG. 3 is a schematic view of a first embodiment of a camera according to the principles of the present disclosure.

With reference now to FIG. 3, an illustrative depiction of a camera 10 is provided. The camera 10 includes a camera head unit 12 and a display control unit 14. The camera head unit 12 includes a camera head 16 and a camera control unit 18. The camera head unit 12 is configured to obtain image data and process the image data into a video signal, as explained in greater detail below. The camera head 16 may be coupled to an endoscope 10a by optics including a plurality of lenses 10b. For illustrative purposes, a description of the camera 10 is provided within the context of an endoscope 10a; that is, the camera 10 forms a single piece of equipment when attached to the endoscope 10. It should be appreciated that other scopes may be used with the camera head 16, illustratively including an exoscope, borescopes and the like. Alternatively, the camera 10 and the endoscope 10a may be formed as a single unit, commonly referred to as a videoscope.

The camera head 16 includes an image sensor 20. The image sensor 20 is fixed within a housing of the camera head 16. The camera head 16 is in communication with the camera control unit 18 through either a cable or a wireless connection. The camera control unit 18 controls various processing functions of the camera head unit 12 such as a readout of the image sensor 20, image focus and the like. The image sensor 20 gathers image data which is processed by the camera control unit 18 to output an image signal. The image signal is processed by the display control unit 14 for display onto a display unit 22. The endoscope 10a and camera head 16 may form an integral unit (commonly known as a videoscope or distal imager endoscope) or may be detached from each other as singular functional pieces. Regardless of the specific configuration, the principles of the present disclosure apply to various examples of video imaging systems 100.

The image sensor 20 can be a complementary metal oxide semiconductor "CMOS" or a charged coupled device "CCD". It should be appreciated that any pixelated image sensor 20 currently known or later developed may be modified and adopted for use herein.

The camera head 16 further includes an inertial movement detection unit 24. The inertial movement detection unit 24 is configured to detect the spatial orientation of the camera head 16 and the endoscope 10a. For example, the inertial movement detection unit 24 may include an accelerometer 26. Any accelerometer 26 currently known and/or later developed may be adapted for use herein. The accelerometer 26 may be mounted to the camera head 16 or endoscope 10a and may detect an acceleration of the camera 10 made in reference to gravity.

In another example of an inertial movement detection unit 24, the inertial movement detection unit 24 includes a gyroscope sensor 28 configured to provide a rotational relationship of the camera 10. In particular, the rotational relationship includes the orientation and angular velocity of the camera head unit 12. Preferably, the gyroscope sensor 28 is one of a plurality of electric devices currently known and/or later developed configured to detect orientation and angular velocity, illustratively including solid state ring lasers, fiber optic gyroscope and/or a quantum gyroscope. The gyroscope sensor 28 may be mounted to the camera head unit 12 and may detect an acceleration of the camera 10 made in reference to the Earth's gravity. In another embodiment, the inertial movement detection unit 24 includes both an accelerometer 26 and a gyroscope sensor 28.

A first input 30 is configured to record the spatial information of the image. The first input 30 may be a button or a touch screen mounted to an outer surface of the camera head unit 12. Alternatively, the first input 30 may be a microphone and a voice recognition unit configured to receive an audible command and record the spatial information of the image upon receipt of the audible command. FIG. 3 depicts that the first input 30 may also be disposed on the display unit 22.

The display control unit 14 is electrically coupled to the camera head unit 12. The display control unit 14 is configured to process the spatial orientation recorded by the first input 30 and the vector information so as to retain a preferred orientation of the image as the camera head unit 12 is moved. An example of a preferred orientation of the image may be an image that is retained in an upright position. As such, the video image displayed by the display unit 22 remains upright as the camera 10 is passed from a nurse to a surgeon.

In another aspect of the camera 10, the camera 10 includes a second input 32. The second input 32 may be a dial, a button assembly, or implemented in a touch screen or the like. The second input 32 may be disposed on a housing of the camera 10, or on the display unit 22. The second input 32 is configured to manually adjust the orientation of the image which was set to the preferred orientation by the camera 10, so as to define an adjusted image orientation.

The camera 10 may be further configured to retain the image in the adjusted image orientation. For example, the display control unit 14 processes the spatial orientation and vector information to orient the image in the preferred orientation. However, there may be an instance where the surgeon prefers an orientation other than the preferred orientation. As such, the second input 32 allows the surgeon to adjust the preferred orientation to a desired orientation (the adjusted image orientation) by actuation of the second input 32.

The camera 10 may further include a memory 34 configured to store the adjusted orientation. The control display unit 22 may be further configured to process the memory 34 so as to automatically adjust the image to the adjusted image orientation. The memory 34 may be disposed in the display control unit 14 or may be disposed on the camera head unit 12. The second input 32 may be further configured to select the adjusted image orientation. It should be appreciated that the description of the camera 10 is provided within the context of a still image for illustrative purposes only and that the camera 10 may be configured to provide a video image using the same principles described above with modifications known to those skilled in the art. For example, the camera control unit 18 processes the image data to generate a video signal, and the display control unit 14 processes the video signal to generate a video image onto the display unit 22.

Figure 4:
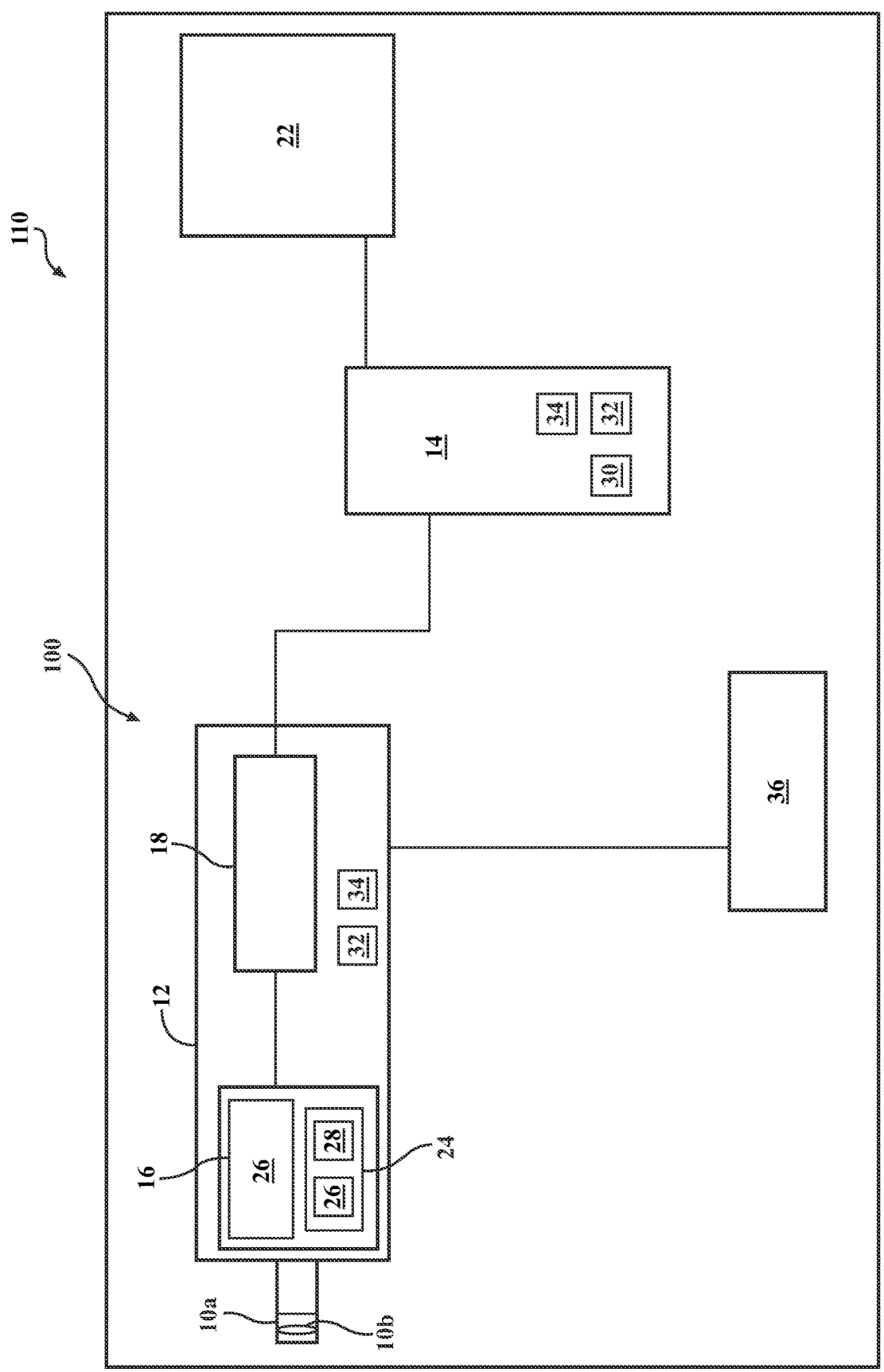
FIG. 4 is a schematic view of an imaging system according to the principles of the present disclosure.

With reference now to FIG. 4, a video imaging system 100 is provided. For illustrative purposes, a description of the video imaging system 100 is provided within the context of a camera 10 having an endoscope 10a.

The camera 10 includes a camera head unit 12, a display control unit 14 and a light source 36. The camera head unit 12 includes a camera head 16 and a camera control unit 18. The camera head unit 12 is configured to obtain image data and process the image data into a video signal. The camera head 16 is coupled to an endoscope 10a by optics including a plurality of lenses 10b. However, it should be appreciated that other scopes may be used, illustratively including an exoscope, borescopes and the like.

The camera head 16 includes an image sensor 20 and an orientation unit 24. The camera head 16 is in communication with the camera control unit 18 through either a cable or a wireless connection. The image sensor 20 gathers image data which is processed by the camera control unit 18 to output an image signal. The image signal is processed by the display control unit 14 for display onto a display unit 22. The endoscope 10a and camera head 16 may form an integral unit or may be detached from each other as singular functional pieces. Regardless of the specific configuration, the principles of the present disclosure apply to various examples of cameras 10 having scopes.

The camera control unit 18 controls various processing functions of the camera head unit 12 to include timing of the light source 36, readout of the image sensor 20, focus and the like. The image sensor 20 functions in coordination with the light source 36 to gather image data which is processed by the camera control unit 18 to output a video signal. The video signal is processed by the display control unit 14. The display control unit 14 processes the video signal for display onto a display unit 22. The endoscope 10 and camera head 16 may form an integral unit or may be detached from each other as singular functional pieces. Regardless of the specific configuration, the principles of the present disclosure apply to various examples of video imaging systems 100.

The orientation unit 24 is configured to detect the spatial orientation of the camera head unit 12 in the same manner as described above with respect to the endoscope 10. It should be appreciated that the same accelerometer 26 and/or gyroscope sensor 28 described above may be modified for use in the video imaging system 110 described herein.

A first input 30 is configured to record the spatial information of the video image. The first input 30 may be a button or a touch screen mounted to an outer surface of the camera head unit 12 and/or the display control unit 14. Alternatively, the first input 30 may be a microphone and a voice recognition unit configured to receive an audible command and records the spatial information of the video image upon receipt of the audible command.

With reference again to FIG. 4, the display control unit 14 is a separate device which is coupled to the camera head unit 12. The display control unit 14 may be coupled to the camera head unit 12 through a wired connection or wirelessly. The display control unit 14 is configured to process the spatial orientation recorded by the first input 30 and the vector information so as to retain an orientation of the video image as the camera head unit 12 is moved. For example, the orientation of the video image may be retained in an upright position as the endoscope 10a is passed from a nurse to a surgeon.

In another aspect of the video imaging system 100, the video imaging system 100 includes a second input 32. The second input 32 may be disposed on the camera head unit 12 or the display control unit 14. In one example, the second input 32 is a dial, a button assembly, or implemented in a touch screen or the like. The second input 32 is configured to manually adjust the orientation of the video image which was set to the preferred orientation by the display control unit 14, so as to define an adjusted video orientation. The video imaging system 100 may be further configured to retain the video image in the adjusted video orientation. For example, the display control unit 14 processes the spatial information and vector information to orient the image in the preferred orientation. However, there may be an instance where the surgeon prefers an orientation other than the preferred orientation. As such, the second input 32 allows the surgeon to adjust the preferred orientation to a desired orientation (the adjusted orientation) by actuation of the second input 32.

The video imaging system 100 may be further configured to retain the image in the adjusted image orientation. For example, the display control unit 14 processes the spatial information and vector information to orient the image in the preferred orientation. However, there may be an instance where the surgeon prefers an orientation other than the preferred orientation. As such, the second input 32 allows the surgeon to adjust the preferred orientation to a desired orientation (the adjusted image orientation) by actuation of the second input 32.

The video imaging system 100 may further include a memory 34 configured to store the adjusted orientation. The control display unit 22 may be further configured to process the memory 34 so as to automatically adjust the image to the adjusted image orientation. In such an aspect, the second input 32 may be further configured to select the adjusted image orientation. It should be appreciated that the description of the endoscope 10*a* is provided within the context of a still image for illustrative purposes only and that the endoscope 10*a* may be configured to provide a video image using the same principles described above with modifications known to those skilled in the art. For example, the camera control unit 18 processes the image data to generate a video signal, and the display control unit 14 processes the video signal to generate a video image onto the display unit 22.

Figure 5:
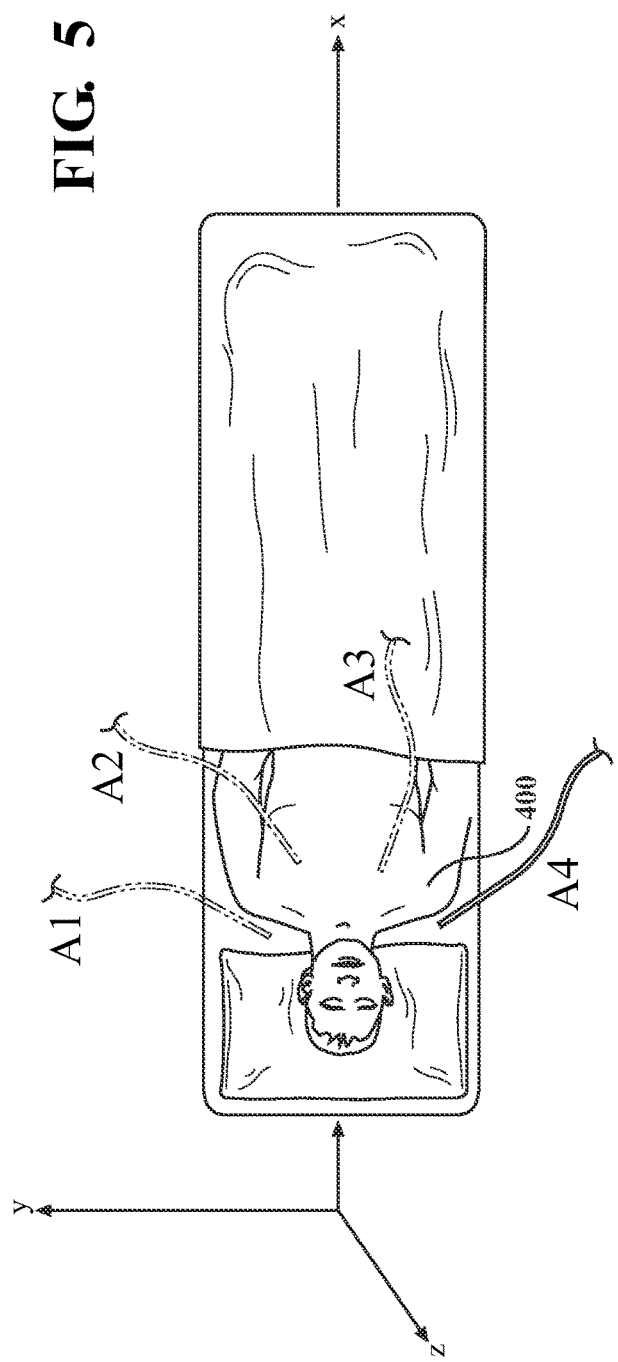
FIG. 5 is a depiction of a surgery room showing the spatial orientation of the camera shown in FIG. 4 as the camera is handed from one person to another.
Figure 6:
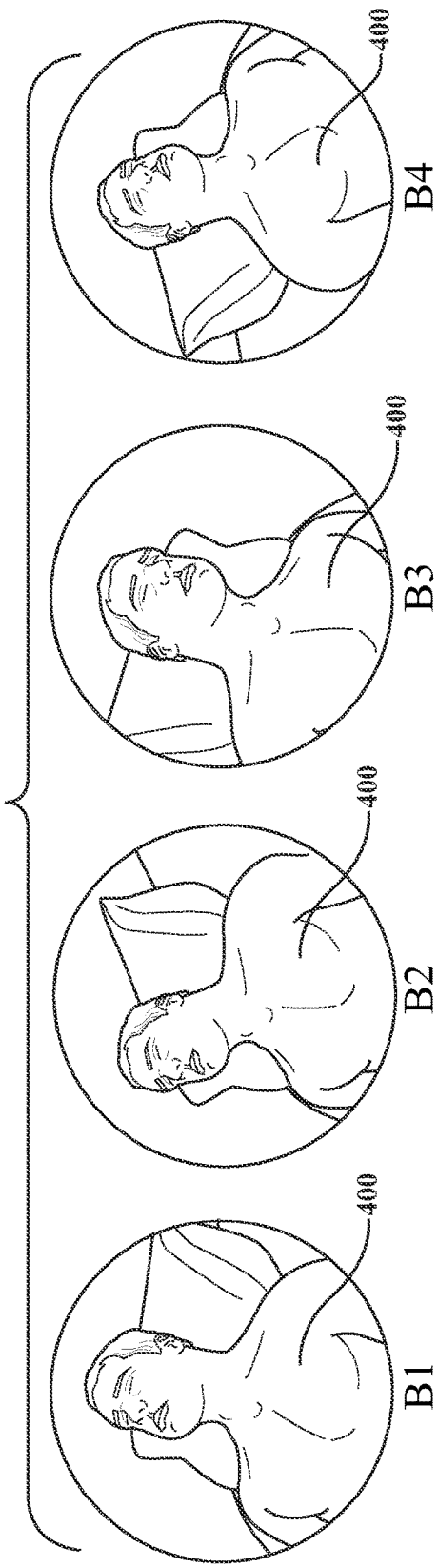
FIG. 6 is a depiction of the video image taken by the camera shown in FIG. 4.

With reference now to FIGS. 5 and 6, a description of the operation of the camera 10 and the video imaging system 100 is provided.

With reference first to FIG. 5, a depiction of the various spatial orientations of the endoscope 10*a* is provided. The spatial orientation as used herein is the position of the endoscope 10*a* with respect to a three dimensional plane, as indicated by axes "X", "Y" and "Z". As shown in FIG. 5, the spatial orientation of the endoscope 10*a* changes, as shown in A1-A4, as the endoscope 10*a* is passed from one user to another.

The inertial movement detection unit 24 is further configured to detect vector information of the endoscope 10*a*. The vector information includes the speed and direction of the camera 10 as the endoscope 10*a* is moved from one position to another. Such information may be obtained by processing the change in the spatial orientation of the endoscope 10*a* with respect to time. The display control unit 14 is configured to process the spatial orientation recorded by the first input 30 and the vector information so as to retain an orientation of the video image as the endoscope 10*a* is moved. For example, the orientation of the video image may be retained in an upright position as the endoscope 10*a* is passed from a nurse 200 to a surgeon 300.

FIG. 6 shows the video image of the camera 10 as the endoscope 10*a* is being handed as shown in FIG. 5. Image B1 is a depiction of the video image taken after the video image is leveled by the user. As used herein, "level" or "leveled" means the orientation of a video image into a preferred orientation. For instance, if the video image is of the surgical room, the video image is rotated so as to have a door in an upright position within the display unit 22.

For illustrative purposes, the endoscope 10*a* is leveled by a nurse 200 and handed over to the surgeon 300. The video image of the camera 10 may be leveled by either physical manipulation of the camera 10, or by manipulation of an actuator, such as a button. Once the video image is leveled, the first input 30 is actuated and the spatial orientation of the endoscope 10*a* is recorded. The leveled video image is the preferred orientation as decided by the nurse 200. At this point, the spatial orientation of the endoscope 10*a* is recorded with respect to the orientation of the video image as seen on the display unit 22.

FIG. 5 shows the endoscope 10*a* moving from the nurse 200 to the surgeon 300. The endoscope 10*a* at A2-A4 has a different spatial orientation relative to the endoscope 10*a* at A1. FIG. 6 shows the video image at B2 and B3 taken at points A2 and A3 of the endoscope 10*a* shown in FIG. 5. Images B2 and B3 are provided to illustrate how the orientation of the video image changes with respect to the leveled orientation set by the nurse. Video image B4 shows that the video image is oriented in the same orientation as video image B1, but taken from a different perspective.

In particular, the display control unit 14 processes the spatial orientation of the endoscope 10*a* by mapping out known reference points taken along the three dimensional plane depicted in FIG. 5. For instance, the center of gravity of the endoscope 10*a* may be at a position "X-a1" along the X axis, a position "Y-b1" along the Y axis and a position "Z-c1" along the Z axis. As the endoscope 10*a* is moved as shown in FIG. 5, the spatial orientation of the endoscope 10*a* changes, for instance the spatial orientation of the endoscope 10*a* at A2 may be a position "X-a2" along the X axis, a position "Y-b2" along the Y axis and a position "Z-c2" along the Z axis, at A3 may be a position "X-a3" along the X axis, a position "Y-b3" along the Y axis and a position "Z-c3" along the Z axis and at A4 may be a position "X-a4" along the X axis, a position "Y-b4" along the Y axis and a position "Z-c4" along the Z axis. The inertial movement detection unit 24 may be further configured to determine how the longitudinal length of the endoscope 10*a* also changes by processing the difference in the spatial orientation at points A2-A4.

As the endoscope 10*a* is moved, the change in the spatial orientation may be processed with respect to time to determine vector information, including the speed, direction and/or acceleration of the endoscope 10*a*. The spatial orientation and vector information, along with the preferred orientation, may be processed by the display control unit 14 to adjust the orientation of video image of the endoscope 10*a* at A4 to the preferred orientation. It should be appreciated that the video image may be processed throughout the process of being handed over, thus the video images B2 and B3 may be displayed on the display unit 22 in the preferred orientation (the orientation shown in images B1 and B4 but with a different perspective), but an actual orientation is shown to provide the reader with an understanding of the concepts disclosed herein.

Moreover, as shown in FIG. 5, the display control unit 14 processes the spatial orientation of the endoscope 10*a* by using a three-dimensional Cartesian coordinate system. Accordingly, as the endoscope 10*a* is moved, its spatial orientation is mapped at predetermined time intervals (i.e., milliseconds, seconds, etc.). For example, the spatial orientation of the endoscope 10, at t=1, may be (0, 4, 4). At t=2, (2, 5, 5). At t=3, (4, 5, 6). Lastly, at t=4, (6, 5, 4). These data points depict the movement of endoscope 10*a* over a known period of time. Subsequently, the speed, velocity, acceleration, and the like of endoscope 10*a* can be calculated by incorporating the data points mapped with respect to time with known mathematical vector equations. Ensuing, a change in the orientation of the image produced by the endoscope 10a can be determined by using the aforementioned calculated results and the data points collected. The orientation of the image produced by the endoscope 10a is capable of being adjusted or corrected. For instance, if the image produced by the endoscope 10a is determined to be incorrectly oriented the image can be adjusted to match a preferred orientation.

As described above, the surgeon 300 may want to further adjust the preferred orientation generated by the display control unit 14 so as to generate an adjusted image orientation. This may be done by the surgeon 300 actuating the second input 32. The camera control unit 18 may include a memory 34 which stores the adjusted image orientation and may automatically adjust the video image to the orientation of the adjusted image orientation.

Figure 7:
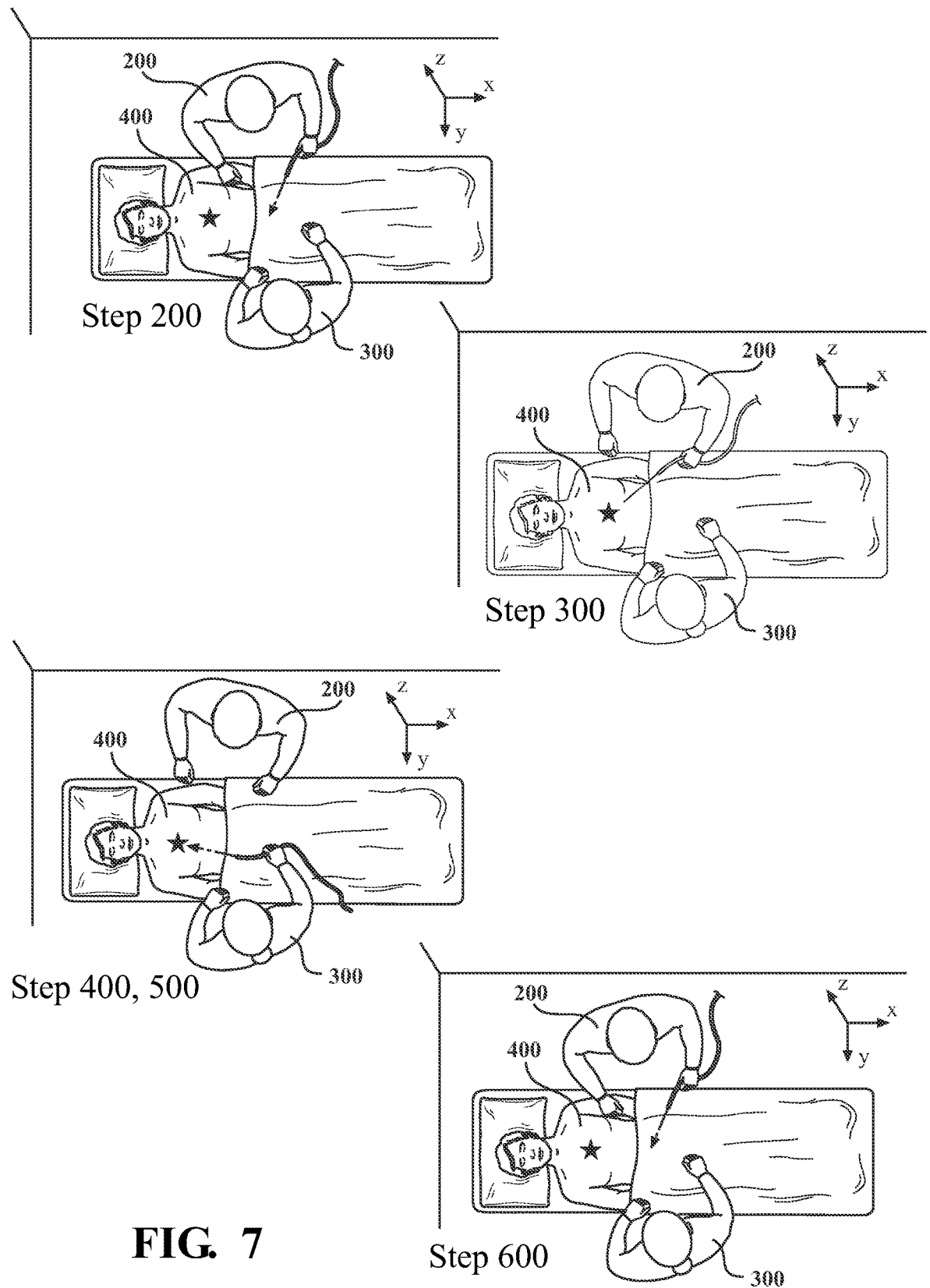
FIG. 7 is an illustration depicting a method for maintaining the orientation of a video image in a preferred orientation according to the principles of the present disclosure.

With reference now to FIG. 7, a method for maintaining an orientation of a video image on a display unit 22 is provided. The method is implemented so as to maintain the video image in an upright position when a video camera 10 is being handed from a first person, such as a nurse, to a second person, such as a surgeon. As used with respect to the method, the term "upright" refers to an orientation as perceived by the end user, in this case the surgeon. That is, it should be appreciated that what may be upright to the nurse 200 may not necessarily be upright as seen by the surgeon 300.

The method includes step 200, pointing the video camera 10 at an end user position and recording a spatial orientation of the video camera 10 when the video camera 10 is pointed at the end user position so as to define a first spatial orientation. The end user position refers to the user who will perform the surgical procedure, in this case the surgeon. The method includes step 300, pointing the video camera 10 at a surgical site and recording the spatial orientation of the video camera 10 when the video camera 10 is pointed at the surgical site so as to define a second spatial orientation. The surgical site refers to the anatomical body part for which a surgical procedure is to be performed.

In this method, the nurse is performing steps 200 and 300. The nurse 200 may actuate a first input 30 that records the respective spatial orientations. The spatial orientations may be captured by the inertial movement detection unit 24 described herein. It should be appreciated that steps 200 and 300 need not be performed in a predetermined sequential order.

The method includes step 400, handing the video camera 10 to the second person, and determining a vector information of the video camera 10 as the video camera 10 is handed to the second person (the surgeon 300). The method may be implemented by a display control unit 14 of the video camera 10. The method includes step 500, processing the first spatial orientation, the second spatial orientation and the vector information so as to maintain the video image in the upright position. Step 500 may be performed by the display control unit 14.

The vector information may be obtained by the inertial movement detection unit 24 as described above. The vector information may be automatically recorded after a second actuation of the first input 30, or may be initiated by a prompt generated by the display control unit 14. For instance, the display control unit 14 may display a prompt which asks "Are you ready to hand the endoscope 10 to the surgeon?", wherein the vector information is recorded when the nurse answers yes. As described above, the vector information includes the speed, direction and/or acceleration.

In another aspect of the method, the method may further step 600, holding the video camera 10 in a use position and recording the spatial orientation of the video camera 10 when the video camera 10 is in the use position so as to define a third spatial orientation. The display control unit 14 is further configured to process the third spatial orientation so as to maintain the video image in the upright position.

A number of implementations have been described. Nevertheless, it will be understood that various modifications may be made without departing from the spirit and scope of the disclosure. Accordingly, other implementations are within the scope of the following claims.

What is claimed is:

1. A camera system configured to display an image onto a display unit as the camera system is handed from a first person to a second person, the camera system comprising:
    a camera head unit having a memory and electric components configured to capture an image, the memory configured to store a preferred orientation of the image established by a user and a second orientation that is different than the preferred orientation, the second orientation being an image of a surgical site;
    an orientation unit disposed on the camera head unit, the orientation unit configured to detect a spatial orientation of the camera head unit and detect vector information of the camera head unit; and
    a display control unit configured to process the vector information detected by the orientation unit and the preferred orientation and the second orientation stored in the memory and process the image so as to adjust an orientation of the image captured by the camera head unit to be oriented in the preferred orientation as the camera head unit is handed from the first person to the second person.

2. The camera system as set forth in claim 1, further including an endoscope attached to the camera head unit, and wherein the image is one of a plurality of images forming a video signal.

3. The camera as set forth in claim 1, further including a first input, the first input configured to provide the preferred orientation.

4. The camera as set forth in claim 1, wherein the orientation unit processes at least one of an acceleration and a gravitational relationship of the camera head unit to determine the vector information.

5. The camera as set forth in claim 4, wherein the orientation unit includes an accelerometer.

6. The camera as set forth in claim 4, wherein the orientation unit includes a gyroscope sensor.

7. The camera as set forth in claim 1, further including a second input configured to manually adjust the orientation of the preferred orientation.

8. The camera as set forth in claim 7, wherein the display control unit is further configured retain the image in the preferred orientation.

9. A method for maintaining an orientation of a video image on a display unit in a preferred orientation, the video image captured by a video camera, the video camera being handed from a first person to a second person, the method comprising the steps of:
    storing a preferred orientation of an image established by a user;
    pointing the video camera at a surgical site by the first person and establishing a second spatial orientation;
    recording the second spatial orientation;
    handing the video camera to the second person;

determining a vector information of the video camera as the video camera is handed to the second person; and providing a display control unit, the display control unit processing the preferred orientation, the second spatial orientation and the vector information so as to maintain the video image in the preferred orientation as the video camera is handed from the first person to the second person.

10. The method as set forth in claim 9, wherein the vector information is determined by at least one of an acceleration and a gravitational relationship of the video camera.

11. The method as set forth in claim 9, further including the step of holding the video camera in a use position and recording a third spatial orientation of the video camera when the video camera is in the use position, wherein the display control unit further processes the third spatial orientation so as to maintain the video image in the preferred orientation.

12. The method as set forth in claim 9, wherein the video camera is an endoscope.

13. The method as set forth in claim 12, wherein the endoscope includes a camera head unit.

14. The method as set forth in claim 13, wherein the camera head unit includes an orientation unit, the orientation unit configured to detect the second spatial orientation.

15. The method as set forth in claim 14, wherein the orientation unit includes an accelerometer.

16. The method as set forth in claim 14, wherein the orientation unit includes a gyroscope sensor.

17. The method as set forth in claim 9, further including a first input configured to manually adjust the orientation of the video image so as to define the preferred orientation.

* * * * *